United States Patent [19]

Moncrief et al.

[11] Patent Number: 5,057,075
[45] Date of Patent: Oct. 15, 1991

[54] METHOD FOR IMPLANTING A CATHETER

[76] Inventors: Jack W. Moncrief, 3711 Greentrails South, Austin, Tex. 78731; Robert P. Popovich, 2928 Kassarine Pass, Austin, Tex. 78704

[21] Appl. No.: 450,055

[22] Filed: Dec. 13, 1989

[51] Int. Cl.$^5$ .................... A61M 31/00; A61M 1/00; A61M 1/28
[52] U.S. Cl. ........................ 604/49; 604/28; 604/29; 604/175
[58] Field of Search ............ 604/49, 52, 53, 28, 604/29, 116, 128, 158, 175, 93

[56] References Cited

U.S. PATENT DOCUMENTS

| 3,752,162 | 8/1973 | Newash ............................ 604/93 |
| 4,392,855 | 7/1983 | Oreopoules et al. ............... 604/175 |
| 4,634,422 | 1/1987 | Kantrowitz et al. ............... 604/49 |
| 4,772,269 | 9/1988 | Twardowski et al. .............. 604/175 |

FOREIGN PATENT DOCUMENTS 2056282 3/1981 United Kingdom ................. 604/28

Primary Examiner—Richard J. Apley
Assistant Examiner—Karen G. Horowitz
Attorney, Agent, or Firm—Arnold, White & Durkee

[57] ABSTRACT

A method for implanting a catheter is disclosed. The method provides for catheter implantation in two stages. Initially, the entire catheter will be implanted in the living body. After sufficient time has passed for tissue in-growth into a portion of the catheter, generally the cuff, an adjacent or nearby portion of the catheter is brought outside the body to facilitate use of the catheter. The catheter preferred for implantation according to the method of the invention has two cuffs, one about 2 to 5 cm in length and the second about 1 to 2 cm in length, an arcuate bend of about 180 degrees, and a coiled tip with side holes.

16 Claims, 2 Drawing Sheets

METHOD FOR IMPLANTING A CATHETER

BACKGROUND OF THE INVENTION

This invention relates to catheters. The invention relates particularly to implantable catheters and a method of implanting catheters in a living body to provide, for example, access to the peritoneal cavity for peritoneal dialysis.

Peritoneal dialysis has long been recognized as a treatment for end stage renal disease but it was not a commonly practiced or preferred treatment until the introduction of Continuous Ambulatory Peritoneal Dialysis ("CAPD"). CAPD is described in U.S. Pat. No. 4,239,041, issued Dec. 16, 1980 to Popovich et al. Before CAPD, the primary problems associated with peritoneal dialysis were recurrent peritonitis and the inefficiency of the dialysis procedure itself, resulting in poor patient rehabilitation.

CAPD is substantially more efficient than earlier methods of peritoneal dialysis and it has increasingly gained popularity as a treatment for end stage renal disease. Also, CAPD to a great extent has solved the problem of progressive uremic syndrome associated with Intermittent Peritoneal Dialysis. However, the risk of infection, particularly peritonitis, associated with peritoneal dialysis remains a problem and is the primary factor inhibiting the commitment of large numbers of patients to peritoneal dialysis, or more particularly, CAPD.

Instances of peritonitis associated with peritoneal dialysis can be most directly attributed to an inadequate bacteriological barrier present in the catheter access to the peritoneal cavity. Efforts to reduce instances of peritonitis have been marginally successful and have dealt primarily with the connection of the dialysis fluid bag to the catheter tubing as described in U.S. Pat. No. 4,620,845 issued Nov. 4, 1986 to Popovich et al. Catheter tunnel and exit site infections remain a problem. There continues to be a need for improved catheters and methods for implanting catheters that result in decreased risk of infection.

SUMMARY OF THE INVENTION

Figure 1:
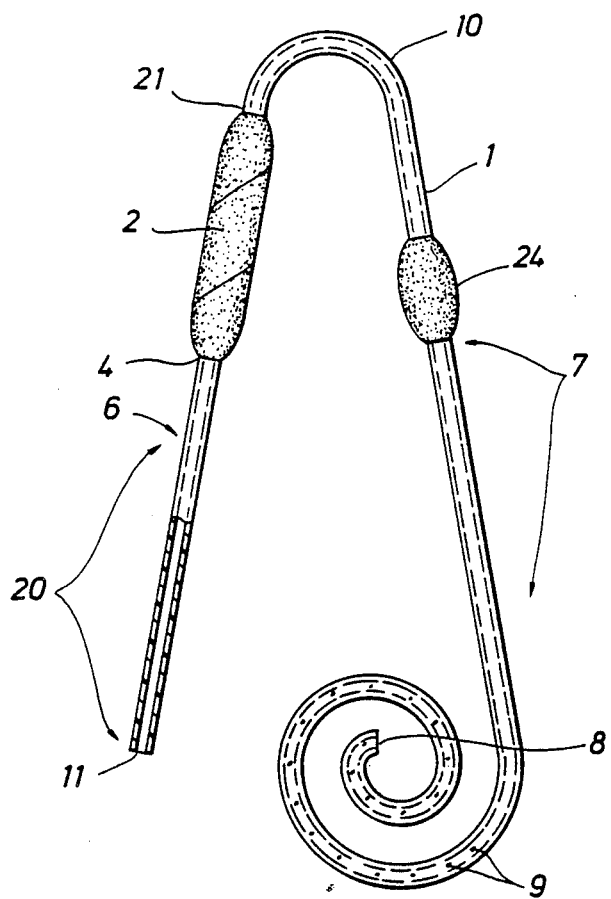
FIG. 1 is a schematic illustration of a catheter suitable for implanting in a living body according to the method of this invention.

The present invention is a method for implanting a catheter in a living body. In the method, an incision is made in the body and the entire catheter is inserted into the body through the incision. The catheter is positioned in the body so that at least a portion of the catheter is in subcutaneous tissue. The incision is then closed and allowed to heal. Subcutaneous tissue is allowed to grow into at least a portion of the catheter, preferably the cuff or cuffs of the catheter. The waiting period for healing and tissue to grow is usually about 1 to 10 weeks, and preferably about 3 to 5 weeks, in length. After this, a smaller incision is made in the body and a portion of the catheter is brought out through it. This external portion may then be connected to a source of fluid, power, or a desired apparatus to accomplish the purpose of the catheter.

This method is particularly suited for implanting catheters to be used for peritoneal dialysis or for providing access to a particular mechanism of the body, such as a circulation system, or an internal, artificial or transplanted organ.

Preferred catheters for implantation according to the method of this invention are comprised of materials that are biocompatible with a segment or segments which are amenable to in-growth of living tissue. An example of such in-growth material is Dacron®. Preferably, such material will comprise a cuff portion or portions of the catheter.

Most preferably, the catheter for implantation according to the method of this invention will have two cuffs, an external (skin) cuff preferably comprised of Dacron®, and a second cuff, also preferably comprised of Dacron®. This second cuff is called the peritoneal cuff when it is to be located at the point where the catheter enters in the peritoneal cavity, as when the catheter is to be used in peritoneal dialysis. The remaining portions of the preferred catheter is comprised of a silicone rubber, preferably Silastic® material. The catheter will also preferably be the "swan-neck" type, having an arcuate bend of about 50 to 180 degrees.

For use in peritoneal dialysis, the catheter is hollow, like a tube, and may be comprised of tubing, with a hole at each end for entry and exit of fluid. The portion of the catheter that will be implanted when the catheter is used may have a coiled tip with side holes for entry and exit of fluid, as well. For use in some other applications, the hollow of the catheter may contain or be at least partially filled with air or electrical materials for conduction of power.

DETAILED DESCRIPTION OF PREFERRED EMBODIMENT

We have discovered an improved method (or process) for implanting a catheter in a living body. The method significantly reduces or alleviates the likelihood of complications associated with catheters, particularly complications such as catheter tunnel infections, at times seen when catheters are used in peritoneal dialysis. The method is particularly applicable to implanting catheters in human beings, although it may be applied to implanting catheters in dogs, monkeys, and other animals, as well.

The preferred method of this invention is generally described below, with respect to a catheter used to provide access to, for example, the peritoneal cavity of a human patient.

Preparing the Patient

To accomplish catheter implantation in the peritoneal cavity according to the method of this invention, the patient is preferably first prepared for surgery. The patient's bladder should be empty and the abdomen preferably shaved and surgically prepared, as standard in the medical field, from xiphoid to symphysis with particular attention to the umbilicus. The abdominal wall must be free of infection. As with any peritoneal catheter insertion, the presence of ileus or extensive previous surgery, with or without infection, necessitates greater precautions because of the increased risk of bowel perforation.

Arrangement should be made for sterile technique, as standard in the medical field. Typically, the physician will wear a sterile cap, mask, gown, and gloves, and the patient will wear a sterile mask or the sterile field at the site and adjacent to the site of the surgery will be appropriately shielded. The patient may be placed under local or general anesthesia.

Selecting and Preparing the Catheter

The method of this invention may be used to implant any catheter the portion or portions of which are comprised of a material to or in which human tissue may attach or grow. Examples of such materials are Dacron ®, a registered trademark of E.I. DuPont de Nemours Company, and Gortex ®, a registered trademark of Gortex Corporation. Suitable catheters will typically have one or more cuffs comprised of such a material.

A preferred catheter for implanting according to the method of this invention is the catheter having the characteristics described below and depicted schematically in FIG. 1. This catheter is particularly suitable for use in peritoneal dialysis.

The catheter illustrated in FIG. 1 is comprised of a hollow tube 1 of silicone rubber, preferably a Silastic ® material. The diameter of the hollow tube depends on the purpose of the catheter but for peritoneal dialysis is preferably about 0.3 cm. Referring to FIG. 1, the tube preferably includes a double cuff 2 and 24, although a single cuff 2 would also be feasible.

The external (skin) or subcutaneous cuff 2 will preferably be about 1.0 to 5.0 cm in length and tapered on each end, 4 and 21. The peritoneal cuff 24 is preferably about 0.5 to 2.0 cm in length and is also tapered on each end. It is located on the catheter immediately distal to the intraperitoneal segment 7. The cuffs 2 and 24 are comprised of a material, preferably Dacron ®, which is amenable to in-growth of human tissue. The cuffs 2 and 24 may be attached to the tube 1 as a coating or the cuffs may themselves be hollow, like a tube, and be attached or connected to the tube 1 comprising the remainder of the catheter. The tube 1 itself may be a single tube or multiple tubes connected together.

A portion or segment 20 of the catheter will be external to the living body, after exteriorization of the catheter is complete and the catheter is ready for use. The subcutaneous cuff 2 will preferably terminate about 1½ to 2 cm from the site 6, where the portion or segment 20 will exit the body. In another embodiment, this cuff will extend the entire length of the portion 10 of the catheter.

The external or exteriorized portion or segment 20 is preferably about 1 to 12 cm in length with a preferred length of 6 to 8 cm. An adaptor or connector may be used to add additional tubing to the segment 20 after exteriorization to increase the length as may be needed to facilitate the purpose of the catheter. For peritoneal dialysis, the end of the external segment will preferably be attached, connected, or fitted directly or indirectly via additional tubing to a source of dialysis fluid, such as a dialysis bag, or to an "artificial tubule" such as that described in U.S. patent application No. 278,241, of Popovich et al., filed Nov. 30, 1988. An adaptor or connector may be used to accomplish such attachment, connection or fit.

The cuffs 2 and 24 and remaining portion of the catheter will be internal to the living body after implantation and exteriorization of portion or segment 20 of the catheter is complete and the catheter is ready for use. For application in peritoneal dialysis, the internal portion of the catheter are together, preferably about 10 to about 40 cm in length. In the average adult, the preferred catheter internal length is about 20 cm. The tip 8 is preferably coiled and has pin holes or side holes or apertures 9 in at least one side of the catheter. The internal portion or segment 10 of the catheter nearest the posterior end 21 of the subcutaneous cuff 2 is bent in an arcuate bend, preferably at about 180 degrees. When the catheter is used for peritoneal dialysis or CAPD, this arcuate bent portion 10 of the catheter will be positioned in the subcutaneous tissue of the living body, the portion 7 will be positioned in the peritoneal cavity, and the coiled tip 8 will be positioned near or in the pelvic cavity.

The dimensions for the catheter recited above are preferable for catheters to be implanted according to the method of this invention in an adult human being of average or typical size. The catheter may be made smaller, as for use by a child, by proportionally reducing the length of the external or exteriorized segment 20, the internal or interiorized segments 7, 8, and 10 and the cuffs 2 and 24. The diameter of the catheter tubing 1 might also be reduced. The catheter might similarly be reduced in size for use in an animal such as a dog or monkey which is smaller than an adult human being. The catheter might also be increased proportionally in size for an animal larger than an average human being, such as a gorilla. The catheter might also be altered to accommodate the infusion of fluids at very low flow rate (small internal diameter) or electrical leads for power sources.

In preparing a catheter for implantation according to the method of this invention, cuffs 2 and 24 are thoroughly wetted with a saline solution. The solution will preferably not contain any antibiotics. Such wetting may be accomplished in any convenient manner, such as, for example, by soaking or spraying, provided that the wetting is thorough and can be conducted under sterile conditions. The saline solution should itself be sterile.

The catheter should be sterile, with the cuffs preferably wet with saline solution, at the time of insertion and implantation of the catheter into the living body.

Initial Stage of Implanting the Catheter

Figure 2:
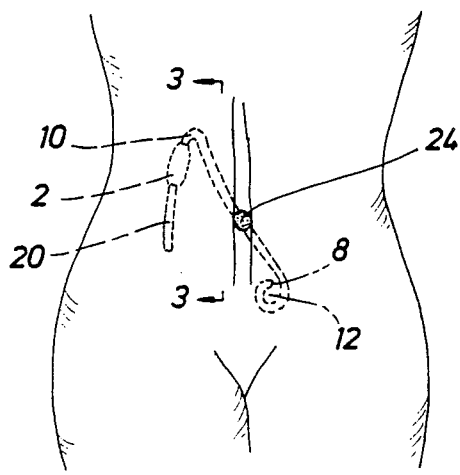
FIG. 2 is a schematic illustration of a catheter for use in peritoneal dialysis at the initial stage of implantation according to the method of this invention.
Figure 3:
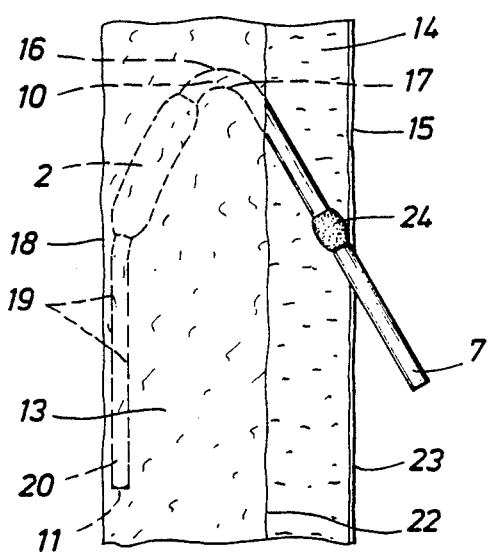
FIG. 3 is an enlarged section of the illustration in FIG. 2 showing a portion of the catheter, including the portion that will ultimately be external the human body when the implantation is complete and the catheter is ready for use.

After preparation of the patient and catheter, in the method of this invention, an incision is made in the abdomen of the patient. The incision is generally through the skin and sufficiently long to allow insertion of the catheter. Preferably the incision will be a 3-4 cm transverse incision, approximately 3 cm below the umbilicus. Referring to FIGS. 2 and 3, the incision is made through the abdominal wall 18, the subcutaneous tissue 13, and the anterior rectus sheath 22. Rectus muscle fibers 14 are dissected bluntly in the direction of its fibers down to the posterior rectus sheath 23. A purse string suture is placed through the posterior rectus sheath 23, transversalis fascia, and the peritoneum 15.

An incision, about 0.5 cm, reaching the peritoneal cavity 5 is made with a scalpel. Care is used to protect the viscera from injury during this maneuver.

The catheter is threaded from a stiffening stylet and introduced deep into the true pelvis 12. It is not necessary to thread the stylet through the entire coiled portion 8. The stylet is removed, and then a syringe containing about 50 cc sterile saline is attached to the tip or end 11 of the catheter, that is, the tip which will ultimately be the external tip of the catheter. The saline is injected into the peritoneal cavity. If the solution does not flow freely, the catheter is repositioned. The purse string is tightened securing the peritoneal cuff 24 immediately anterior to the posterior rectus sheath 23. During implantation, none of the peritoneal cuff 24 material should protrude into the peritoneal cavity. No suture should be placed in the cuff material itself.

A transverse incision (about 1.5 cm) is made approximately 6 cm above the initial incision. A tunnel is made with a trocar in the subcutaneous tissue between the two incisions. The trocar is pulled back and the tunnel is widened bluntly with a long-nosed hemostat from the upper incision to accommodate the subcutaneous cuff 2. The tip 11 of the catheter is grasped with the hemostat and pulled through the tunnel.

A superior subcutaneous pocket is made to accommodate the bent portion 10 of the catheter. After the bent portion 10 is placed in this pocket, allow the external tip 11 to lie on the surface of the skin to determine the natural direction of the subcutaneous tunnel which is to be created next. By blunt probing with a hemostat, a subcutaneous tunnel is created along this path between the upper incision and down to the point where the subcutaneous cuff 2 will lodge. A small counter incision is created about 3-4 cm below the cuff. The tip of the catheter 11 is attached to the trocar and tunnelled down and out through the counter incision. The part of the tunnel between the subcutaneous cuff and the counter incision has a diameter no bigger than that of the catheter.

Downward from the counter incision the subcutaneous tissue is dissected using both sharp and blunt techniques to create a linear subcutaneous space 19 for the external segment of the catheter 20 (about 6 to 8 cm in length). The segment 20 is introduced into this space 19 using a hemostat. This pocket should be adequate in length to admit the entire segment 20 without bending the catheter.

The abdominal wall 18 is closed using standard techniques, such as absorbable suture on the posterior sheath, fascia, subcutaneous tissue, and subcuticular layers. Preferably, routine subcuticular skin closure is placed in the small counter incision. Sterile dressings are applied.

At this stage of the method of the invention, the catheter is now completely under the skin and is easily palpated.

Waiting Period

After the catheter is implanted—completely under the skin —and the incisions closed as described above, the catheter is allowed to reside in the subcutaneous tissue (except for portion 7 in the peritoneal cavity and portion 8 in the pelvic cavity 12) for a period of time. The length of such period of time is usually about 1 to 10 weeks with a preferred period of about 3 to 5 weeks. This waiting period allows for maximum tissue in-growth into the cuffs in a sterile environment.

Final Stage of Implanting the Catheter

After sufficient waiting time with the catheter fully implanted in the subcutaneous tissue 13 (except for portion 7 in the peritoneal cavity and portion 8 in the pelvic cavity), and such that tissue has grown into the cuffs 2 and 24 of the catheter, the portion 20 of the catheter will be ready to be removed from the subcutaneous tissue and brought outside the body to facilitate use of the catheter. Such exteriorization of the catheter may be performed on an outpatient basis using sterile technique under a local anesthetic. The patient is prepped and draped in the usual manner.

Figure 4:
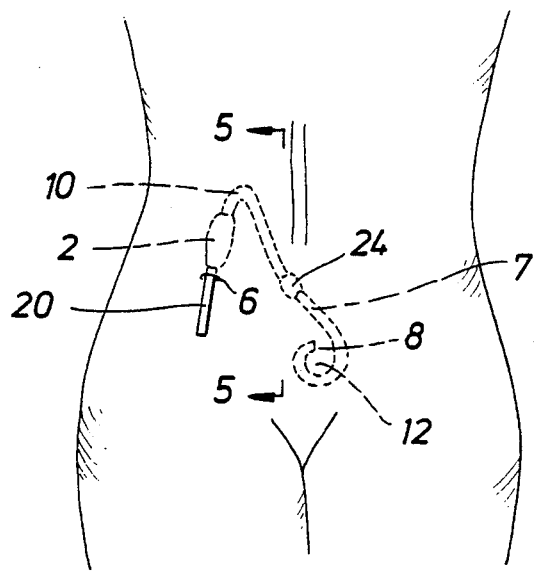
FIG. 4 is a schematic illustration of a catheter for use in peritoneal dialysis at the final stage of implantation in the human body according to the method of this invention.
Figure 5:
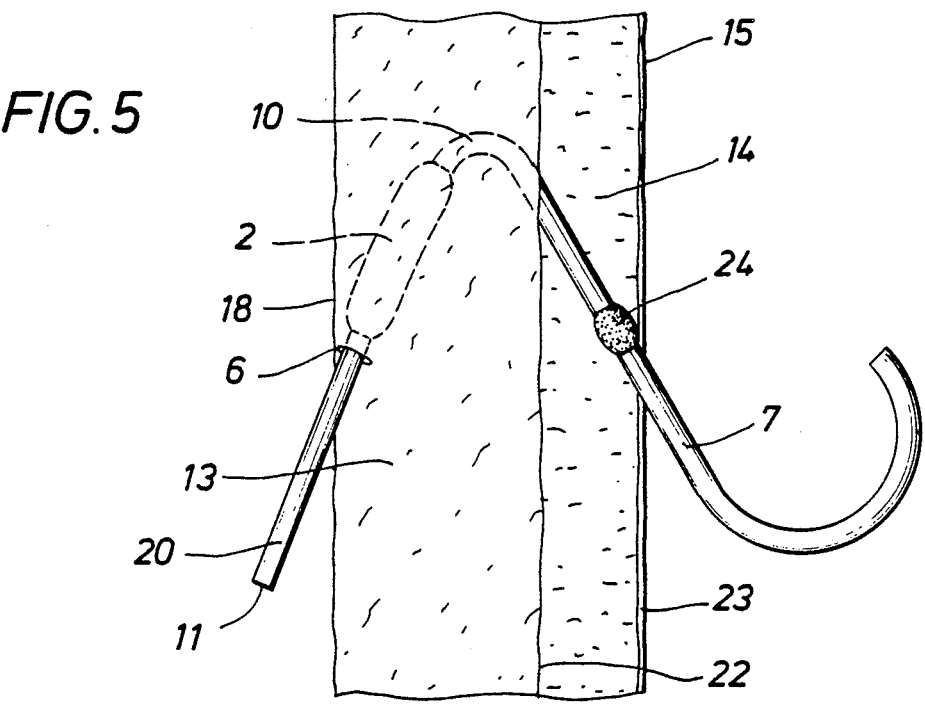
FIG. 5 is an enlarged section of the illustration in FIG. 4 showing a portion of the catheter, including the portion of the catheter that is external the human body.

To accomplish the exteriorization, the end 20 or tip 11 of the catheter is identified. Such identification may be accomplished by palpating the catheter, and particularly by palpating the subcutaneous cuff 2 of the catheter under the skin. Referring to FIGS. 4 and 5, an incision 6 is made, preferably about 2 cm below the edge 4 of the cuff 2. The incision 6 should be sufficiently small, preferably about 0.5 cm, such that sutures will not be required. The end 20 of the catheter is then pulled out of the subcutaneous space or pocket 19 and through the incision to the surface and then outside the skin. The end 20 of the catheter may be pulled from the subcutaneous space or pocket 19 by dissecting the catheter from the subcutaneous tissue bluntly using a curved hemostat or similar instrument and then placing a hemostat under the catheter and rotating the instrument upward, thereby pulling the catheter upward. The pulling will preferably be gentle so as not to significantly disrupt tissue in-growth into the subcutaneous cuff 2.

After exteriorization, the tip 11 and end 20 of the catheter are examined. If mucous or tissue fluid is present, the tip 11 and end 20 should be rinsed with isopropyl alcohol or similar disinfectant fluid and preferably allowed to adequately dry before being used or prepared for use such as by insertion into an adaptor for connection to a dialysis bag or the "artificial tubule" of U.S. patent application No. 278,241, or other preparation for use.

In using the catheter for peritoneal dialysis, titanium or plastic adapters, connected to a source of dialysis solution such as a dialysis bag or the "artificial tubule", are preferred. When the adaptor is inserted and the catheter is connected to the dialysis bag, some tension should preferably be applied to the end 20 of the catheter to insure that a good seal is present. A small amount of dialysate (approximately 100 cubic cm) may be infused under low pressure and allowed to drain to facilitate drainage of any fibrinous material that may have accumulated in the catheter. Dialysis may then begin.

Although the principles of the method of this invention have been described with respect to subcutaneous access to the peritoneal cavity, the method of the invention may be applied as well to access other mechanisms or other cavities of a living body. For example, the method of implanting a catheter according to the method of this invention may be used for catheters to allow infusion or drainage of cavities or semipermanent access to a circulation system, such as the vascular circulation, and the central nervous system fluid circulation. The method of this invention may also be used for implanting catheters to provide transcutaneous access for artificial organ procedures, such as a power supply to an artificial heart. The catheter would be attached to such mechanisms to accomplish such access by techniques known to those skilled in the art. Other potential applications for the use of catheters implanted according to the method of this invention include, but are not limited to, the following:
1. subclavian catheter access
2. femoral vein catheter access
3. adjacent vein catheter access
4. transperitoneal hyperalimentation
5. enteral feeding access
6. esophageal bypass access
7. tracheal bypass access
8. power to intra-aortic balloon pulsation access
9. power to artificial heart access
10. power to left ventricular assist device access
11. subcutaneous monitoring device
12. any other transcutaneous system
13. access to cerebral spinal fluid
14. access to an internal organ
15. access to an artificial internal organ
16. access to a transplanted organ
17. access to an infusion pump

EXPERIMENTAL

Catheters have been implanted according to the method of this invention in both animal and human patients. These experiments dealt primarily with the lapse of time necessary to establish firm tissue in-growth into the catheter cuff and the patency of the catheter present in body tissue for the extended period required for tissue in-growth.

Catheter exit site infections are one of the common sources for bacterial invasion of the catheter tunnel and subsequently into the peritoneal cavity thus causing peritonitis. Peritonitis is the inflammation of the peritoneum, the membranous coat lining the abdominal cavity and infesting the viscera. The design of the preferred catheter for implantation according to the method of this invention offers a bacteriological barrier created by tissue in-growth into the subcutaneous cuff when implanted according to the method of this invention. In addition to the subcutaneous cuff, there is a peritoneal cuff located immediately proximal to the intraperitoneal segment of the catheter. With adequate tissue in-growth into this cuff, peritoneal leakage should not occur or at least should be substantially and significantly reduced.

Fifteen catheters with a subcutaneous cuff, but not a peritoneal cuff, were implanted according to the method of this invention utilizing a canine model. The implantation and exteriorization techniques were conducted as described earlier. Catheter exit site infections were not observed, but some interstitial edema in the tissues surrounding the subcutaneous cuff occurred. This edema is thought to have been due to dialysate transferring from the peritoneal cavity down the outside of the catheter to these tissues. This occurrence prompted the addition of the peritoneal cuff.

Twenty-eight catheters have been implanted in human patients according to the method of this invention. Since implantation, catheters in seven of the patients have been removed due to complications. One of the seven patients, an insulin requiring diabetic, had a catheter tunnel infection including the cuff. The course of infection was marked by four episodes of peritonitis prior to the removal of the catheter. Two other patients had complications caused by a pre-existing condition known as ascites, excessive accumulation of serous fluid in the peritoneal cavity. This fluid prevented any tissue in-growth into the cuff material. The fourth patient had had extensive abdominal surgeries resulting in massive adhesions, the abnormal joining of organs or structures to each other. This condition severely reduced the capacity of the peritoneal cavity for receiving or dwelling volumes of dialysate necessary for peritoneal dialysis. Two of the patients had catheters removed as a result of renal transplantation, but both were functioning catheters at the time. One catheter was removed because of abdominal hernia.

The remaining catheters have functioned well with reports of only 2 cases of peritonitis. Both of these cases of peritonitis were clearly identified to be the result of technique/contamination during actual dialysis exchanges by the patients and were not related to exit site or tunnel infections.

This clinical evidence demonstrates improvement in catheter function with catheter implantation according to the method of this invention, as compared to previous methods of implanting catheters and use of catheters, with only a subcutaneous cuff, in which exit site and tunnel infections are common.

The principle of the invention and the best mode for applying that principle have been disclosed. It is to be understood that the foregoing is illustrative only and that variations and modifications can be employed without departing from the scope of the invention defined in the following claims.

What is claimed is:

1. A method for implanting a catheter in a living body, wherein said catheter consists of a hollow tube with an arcuate bend between a subcutaneous cuff and a peritoneal cuff, with end portions of said catheter extending from said cuffs, and said cuffs are comprised of a biocompatible material amendable to in-growth of living tissue, said method comprising:
   making a first incision in said body;
   inserting the entire catheter through said incision into said body;
   positioning the catheter in said body such that the peritoneal cuff is near but does not protrude into the peritoneal cavity;
   making a second incision in said body near said first incision;
   making a subcutaneous tunnel between said first and said second incisions, thereby forming a pocket in said tissue sufficient to accommodate the arcuate bend portion of the catheter;
   positioning said arcuate bend portion of the catheter in said tunnel with said subcutaneous cuff adjacent subcutaneous tissue;
   positioning said catheter end portion extending from said subcutaneous cuff such that said end is adjacent subcutaneous tissue;
   closing the incisions such that the entire catheter is implanted inside the body;
   allowing the site of said incisions to heal;
   allowing subcutaneous tissue to grow into said cuffs;
   making an incision in the body smaller that the first incision and near the subcutaneous cuff such that the end portion of the catheter adjacent the subcutaneous cuff may be brought outside the body through said incision; and
   bringing outside the body through said smaller incision the end portion of the catheter adjacent the subcutaneous cuff without substantially disturbing tissue in-growth into the subcutaneous cuff and leaving inside said body the portions of the catheter including the subcutaneous cuff, the arcuate bend and the peritoneal cuff.

2. A method for implanting a catheter in a living body for access to a cavity in said body, wherein said catheter comprises a hollow tube with a subcutaneous cuff near one end of said catheter, said cuff being comprised of a biocompatible material amenable to in-growth of living tissue, said method comprising:
   making an incision in said body;
   inserting the entire catheter through said incision into said cavity of the body;
   positioning the catheter such that the subcutaneous cuff is adjacent subcutaneous tissue and the end of the catheter, which is adjacent said cuff, is adjacent subcutaneous tissue;
   closing the incision; such that the entire catheter is implanted inside the body;
   allowing the site of said incision to heat;
   allowing the subcutaneous tissue to grow into said subcutaneous cuff;
   making a smaller incision in the body near the catheter; and
   brining outside the body through said smaller incision the end of the catheter near the subcutaneous cuff, said end having been positioned inside and adjacent subcutaneous tissue adjacent said cuff, without substantially disturbing the tissue in-growth in said subcutaneous cuff and without externalizing the subcutaneous cuff.

3. A method for implanting a catheter in a living body for access to a mechanism of said body, wherein a portion of said catheter comprises a cuff of material amenable to in-growth of living tissue and said cuff is not at an end of such catheter, said method comprising:
   making an incision in said body;
   inserting the entire catheter through said incision into said body;
   positioning the portion of the catheter comprising a cuff and an end of the catheter in subcutaneous tissue, and attaching a different portion of said catheter to said mechanism;
   closing the incision such that the entire catheter is implanted inside the body;
   allowing the site of the catheter insertion to heal;
   allowing subcutaneous tissue to grow into said cuff;
   making a smaller incision in the body near the catheter; and
   bringing outside the body through said smaller, incision the end of said catheter which was positioned adjacent subcutaneous tissue nearest said cuff without externalizing the cuff and without substantially disturbing the tissue in-growth in said cuff.

4. The method of claim 3 wherein said mechanism of the body is a circulation system.

5. The method of claim 4 wherein said circulation is vascular circulation.

6. The method of claim 4 wherein said circulation is central nervous system fluid circulation.

7. The method of claim 3 wherein said mechanism of the body is an artificial internal organ.

8. The method of claim 3 wherein said mechanism of the body is an internal or transplanted organ.

9. The method of claim 3 wherein said mechanism of the body is an infusion pump.

10. A method for implanting, in a peritoneal cavity of a living body, a catheter having a portion to be external and a portion to be internal the body, said portion to be internal comprising at least one cuff of biocompatible material amenable to in-growth of living tissue, said method comprising:
    making an incision in the abdomen of said body;
    inserting the entire catheter through said incision into said peritoneal cavity;
    positioning the catheter portion to be external and an adjacent part of the catheter portion to be internal, including said catheter portion comprising a cuff of biocompatible material amenable to in-growth of living tissue, directly in a pocket of subcutaneous tissue such that the catheter portion to be external is adjacent subcutaneous tissue;
    positioning the remaining portion of the catheter to be internal in the peritoneal and pelvic cavities of the body;
    closing the incision such that the entire catheter is implanted inside the body;
    allowing the incision to heal;
    allowing subcutaneous tissue to grow into said cuff portion of the catheter;
    making a smaller incision in the abdomen of the body near the catheter; and
    bringing out through said smaller incision the external portion of the catheter without substantially disturbing the tissue in-growth into said cuff.

11. The method of claim 10 wherein said cuff extends at least a portion of the length of the catheter portion which remains internal the body in said pocket of subcutaneous tissue and tissue in-growth occurs along the length of the cuff.

12. The method of claim 10 wherein said catheter comprises two cuffs—a subcutaneous cuff and a peritoneal cuff—comprised of biocompatible material amendable to the in-growth of living tissue.

13. The method of claim 10 further comprising attaching to said external portion of the catheter a source of peritoneal dialysis fluid.

14. The method of claim 10 further comprising attaching to said external portion of the catheter a container for spent dialysis fluid.

15. A method for implanting, in a peritoneal cavity of a living body, a catheter having at least one cuff comprised of biocompatible material amenable to the in-growth of living tissue, a portion anterior the cuff to be external the body after implantation of the catheter, and a portion posterior the cuff to be internal the body after implantation of the catheter, comprising:
    making an incision in the abdomen of said body;
    inserting the entire catheter through said incision into said peritoneal cavity;
    positioning the cuff and anterior portion of the catheter in a space of subcutaneous tissue adjacent said peritoneal cavity such that both the cuff and the anterior portion of the catheter are adjacent subcutaneous tissue;
    positioning the tip of the posterior portion of the catheter in the peritoneal cavity of the body;
    closing the incision such that the entire catheter is implanted in the body;
    allowing subcutaneous tissue to grow into said cuff for about 1 to 10 weeks;
    making a smaller incision in the abdomen of the body near the cuff adjacent to the skin;
    bringing outside the body through said smaller incision the anterior portion of the catheter except for a portion about 1½ to 2 cm adjacent the cuff, without substantially disturbing the in-growth of tissue in said cuff.

16. The method of claim 2 wherein the catheter, after insertion into the body, is positioned such that subcutaneous tissue surrounds the entirety of the subcutaneous cuff and portion of the catheter immediately adjacent the cuff.

* * * * *

UNITED STATES PATENT AND TRADEMARK OFFICE
CERTIFICATE OF CORRECTION

PATENT NO. : 5,057,075

DATED : October 15, 1991

INVENTOR(S) : Jack W. Moncrief and Robert P. Popovich

It is certified that error appears in the above-identified patent and that said Letters Patent is hereby corrected as shown below:

Column 8;

In claim 2, at line 14, the semicolon after "incision" should be deleted, and at line 16, the word "heat" should read --heal--.

Column 10;

In claim 12, at lines 29-30, the word "amendable" should read --amenable--.

Signed and Sealed this

Twenty-third Day of March, 1993

Attest:

STEPHEN G. KUNIN

*Attesting Officer*   *Acting Commissioner of Patents and Trademarks*

UNITED STATES PATENT AND TRADEMARK OFFICE
CERTIFICATE OF CORRECTION

PATENT NO. : 5,057,075
DATED : October 15, 1991
INVENTOR(S) : Jack W. Moncrief and Robert P. Popovich It is certified that error appears in the above-identified patent and that said Letters Patent is hereby corrected as shown below:

Column 8, at line 33, the word "amendable" should read --amenable--.

Column 9, at line 45, the comma after "smaller" should be deleted.

Signed and Sealed this

Twenty-third Day of November, 1993

Attest:

BRUCE LEHMAN

*Attesting Officer*        *Commissioner of Patents and Trademarks*

UNITED STATES PATENT AND TRADEMARK OFFICE
CERTIFICATE OF CORRECTION

PATENT NO. : 5,057,075

DATED : October 15, 1991

INVENTOR(S) : Jack W. Moncrief, et. al.

It is certified that error appears in the above-identified patent and that said Letters Patent is hereby corrected as shown below:

Column 9, Claim 2, line 14, the semicolon after "incision" should be deleted, and at line, the word "heat" should read --heal--.

Column 10, Claim 12, lines 29-30, the word "amendable" should read --amenable--.

This certificate supersedes Certificate of Correction issued March 23, 1993

Signed and Sealed this

Twenty-second Day of February, 1994

Attest:

BRUCE LEHMAN

Attesting Officer

Commissioner of Patents and Trademarks